US009183720B2

(12) United States Patent
Miladin et al.

(10) Patent No.: US 9,183,720 B2
(45) Date of Patent: *Nov. 10, 2015

(54) INTERACTIVE MEDICAL DEVICE MONITORING AND MANAGEMENT SYSTEM

(71) Applicant: DocView Solutions LLC, Cherry Hill, NJ (US)

(72) Inventors: John D. Miladin, Medford, NJ (US); Steven A. Landau, Voorhees, NJ (US); Kostas Ilias Nasis, Woodbury, NJ (US)

(73) Assignee: DocView Solutions LLC, Cherry Hill, NJ (US)

( * ) Notice: Subject to any disclaimer, the term of this patent is extended or adjusted under 35 U.S.C. 154(b) by 68 days.

This patent is subject to a terminal disclaimer.

(21) Appl. No.: 14/074,838

(22) Filed: Nov. 8, 2013

(65) Prior Publication Data
US 2014/0062694 A1 Mar. 6, 2014

Related U.S. Application Data

(63) Continuation-in-part of application No. 13/692,364, filed on Dec. 3, 2012.

(60) Provisional application No. 61/586,741, filed on Jan. 14, 2012.

(51) Int. Cl.
*G08B 1/08* (2006.01)
*G08B 21/02* (2006.01)
*G06F 19/00* (2011.01)

(52) U.S. Cl.
CPC ............. *G08B 21/02* (2013.01); *G06F 19/325* (2013.01); *G06F 19/345* (2013.01); *G06F 19/3418* (2013.01); *G06F 19/3487* (2013.01); *G06F 19/363* (2013.01)

(58) Field of Classification Search
CPC .................................................. G06F 2201/20
USPC ............... 340/539.1, 539.11, 539.12, 539.13, 340/506, 3.1, 573.1
See application file for complete search history.

(56) References Cited

U.S. PATENT DOCUMENTS

2008/0300572 A1* 12/2008 Rankers et al. ............... 604/504
2011/0119080 A1* 5/2011 Hayter et al. .................. 705/2

* cited by examiner

*Primary Examiner* — Daryl Pope
(74) *Attorney, Agent, or Firm* — Dinsmore & Shohl LLP

(57) ABSTRACT

A system for improving medical device management for a patient is also provided. The system can include a portable wireless device having an ECU, memory and an interactive remote patient monitoring module (IRPMM) for at least one medical device. The IRPMM has a medical device data request module that is operable to request and receive medical device data input from the at least one medical device. The medical device data can be input by the patient, or in the alternative, be automatically received without input from the patient. The IRPMM also has a medical device data supply module receives medical device information from an outside third party and provides the medical device information to the patient.

10 Claims, 17 Drawing Sheets

Fig-4

DOC VIEW

COPD

Begin Check - in >
Last check - in 1/5/12 10:51 PM

Send a message >
Is there anything you need help with ?

Recent activity

| 2.5 | January 5, 2012   10:51 PM | > |
| | Is there anything you need help with ? | |
| 0.0 | January 5, 2012   6:41 PM | > |
| | Response received | |
| 1.0 | January 5, 2012   6:01 PM | > |
| | Response received | |

View Older Reports >
27 more

Feedback & Technical Assistance

Fig-5

DOC VIEW

Breathlessness

| 0 | 0.5 |
| none | very mild |
| 1 | 2 | 3 |
| less mild | mild | more mild |
| 4 | 5 | 6 |
| less moderate | moderate | more moderate |
| 7 | 8 | 9 |
| less severe | severe | more severe |
| 10 |
| extremely |

Previous | Next

Fig-6

DOC VIEW

Sputum Quantity

None

< 1 Tablespoon

≥ 1 Tablespoon  ✓

> 1/4 Cup

Previous | Next

Fig-7

DOC VIEW

Sputum Quantity

None

White

Yellow  ✓

Green

Brown

Previous | Next

DOC VIEW

| 2.5 Moderate | January 5, 2012 10.51 PM |

Summary

| | |
|---|---|
| Breathlessness | 6 |
| Sputum Quanity | ≥ 1 Tbs. |
| Sputum Color | Green |
| Spuntum Consistency | Thin |
| Peak Flow | 580 |
| Cough ? | Yes |
| Wheeze ? | No |
| Sore Throat ? | |

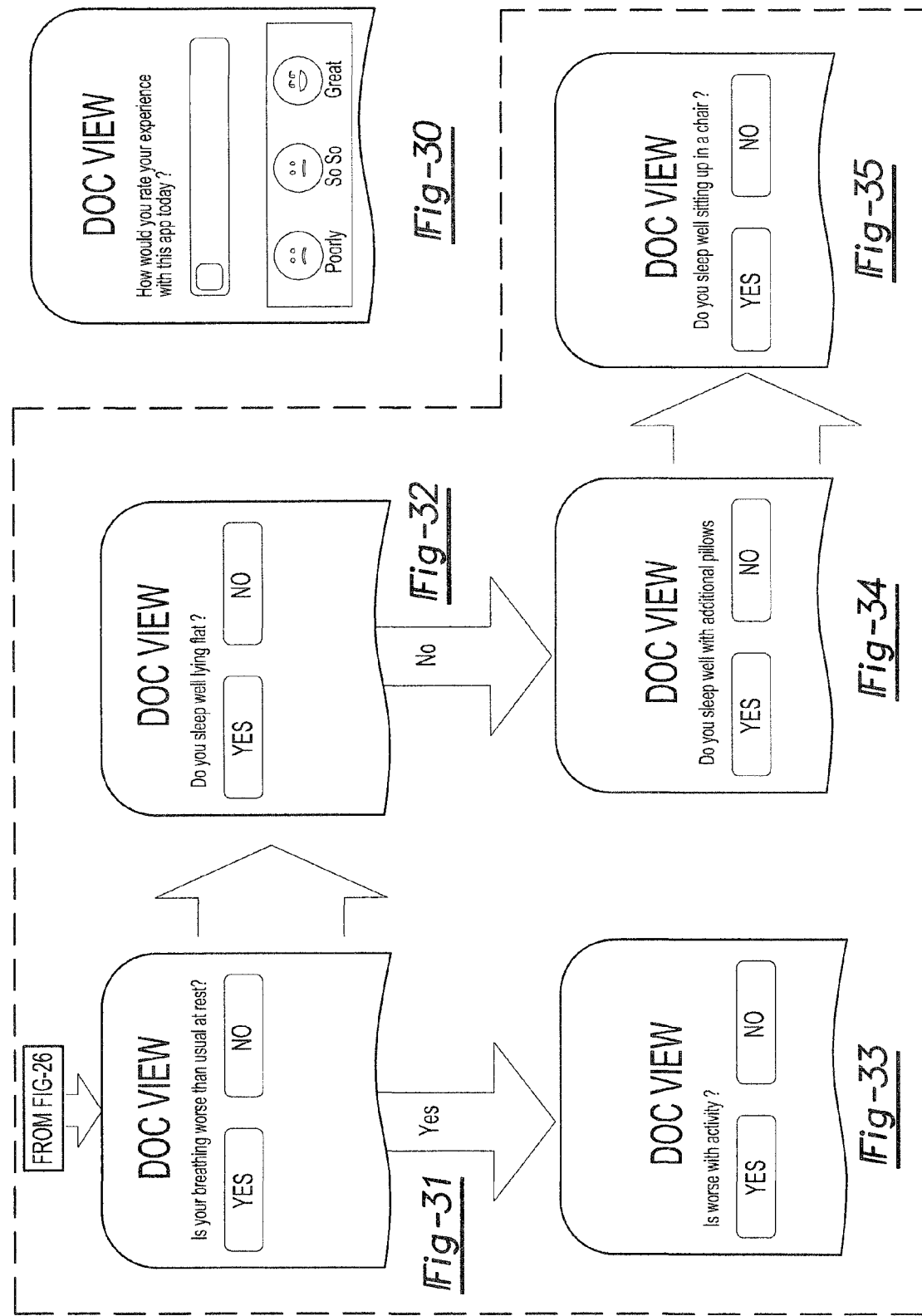

INTERACTIVE MEDICAL DEVICE MONITORING AND MANAGEMENT SYSTEM

CROSS-REFERENCE TO RELATED APPLICATIONS

This application is a continuation-in-part and claims priority to U.S. patent application Ser. No. 13/692,364 filed Dec. 3, 2012, which in turn claims priority to U.S. Provisional Patent Application No. 61/586,741 filed Jan. 14, 2012, both of which are incorporated in their entirety by reference.

FIELD OF THE INVENTION

The present invention is related to a system for improving health management for a patient, and in particular to a system for improving medical device monitoring and management using portable wireless devices and utilizing a specific algorithm or decision tree as part of an interactive remote patient monitoring system.

BACKGROUND OF THE INVENTION

The present health care system is complicated and expensive. Furthermore, typical health care for an individual requires the individual, e.g. a patient, to travel to a doctor's office, urgent care center, and/or a hospital in order to be seen by a doctor, be administered tests, and the like. Such travel for the individual can be difficult and some testing for the patient could be self-administered if monitored or supervised in a desired manner.

According to the Center for Disease Control (CDC), chronic diseases are the leading cause of death in the U.S. In fact, 7 out of 10 deaths among Americans each year are from chronic diseases. Heart disease, cancer and stroke account for more than 50% of all deaths each year. Chronic diseases such as heart disease, stroke, cancer, diabetes, and arthritis are among the most common, costly, and preventable of all health problems in the U.S. The Global Status report said so-called non-communicable diseases accounted for more than 36 m deaths in 2008, and is rapidly rising.

In response to the need of reducing health care costs, remote disease monitoring systems have been attempted. However, heretofore systems still require a nurse and/or doctor to review each and every piece of data provided by a patient in order to prescribe a treatment or treatment plan. Additionally many hospital re-admissions are the direct result of not following the discharge notes or not reacting timely to changes in the patient's condition. Therefore, an improved interactive remote disease monitoring system that can automatically suggest one or more treatment intervention protocols, alert a health care provider of a potential problem with a patient's health and the like would be desirable. Additionally, the system is implemented to create a more personal patient-physician relationship for the Care Coordination Team while encouraging self-management and individual responsibility, and thereby leading to mutual accountability. By creating intelligent, measurable, real-time, and data-driven health outcomes, reduced hospital re-admissions, improved quality of life and effective cost savings opportunities can be provided while at the same time affording better care coordination for nurse/clinician treatment teams and disease-specific self-monitoring and personalized care plans.

In addition to the above, medical devices as defined by the Federal Food, Drug, and Cosmetic Act (FD&C), United States Code 201(h), are known and commonly used in providing health care to patients. For example, it has been estimated that approximately 100,000 defibrillators are implanted in the United States alone each year. Other types of implantable medical devices (IMDs) include pacemakers, insulin pumps, neurostimulators, and the like. In addition, such IMDs can feature wireless communication, however this is not required.

Heretofore systems for monitoring such medical devices have required patients to visit their doctor's office, a hospital, urgent care center, etc. Therefore, an interactive medical device monitoring and management system that provides intelligent, measurable, real-time, and data-driven health decisions would reduce hospital re-admissions and improve quality of life with effective cost savings opportunities for patients. Naturally, such a system would be desirable.

SUMMARY OF THE INVENTION

A system for improving disease and/or medical device management for a patient is provided. The system can include a portable wireless device having an electronic control unit, memory, and an interactive remote patient-monitoring module (IRPMM) for at least one disease and/or at least one medical device. The portable wireless device is operable to transmit and receive information to and/or from an outside third party, the outside third party possibly being a clinician, health care provider, etc. In addition, the IRPMM can have a clinical data and/or medical device data request module that is operable to request and receive clinical data and/or medical device data input from a patient related to at least one disease. The IRPMM can also have a clinical data and/or medical device data supply module that is operable to receive clinical information from the outside third party and provide/supply the clinical information to the patient.

In some instances, the clinical data request module and the medical device data request module are one and the same, however this is not required. Likewise, the clinical data supply module and the medical device data supply module are one and the same, however this is not required In some instances, the system can have one or more certified algorithms and/or decision trees that can receive and process the clinical data and/or medical device input from the patient and provide a preferred method of treatment. In addition, the system can incorporate a health baseline for an individual patient, which in combination with the at least one certified algorithm and/or decision tree can provide a unique output, i.e. interventional method of treatment, for the patient.

The clinical data and/or medical device data request module can ask a plurality of questions tailored to the individual patient, the questions being a function of at least one disease. For example and for illustrative purposes only, the clinical data and/or medical device data request module can ask subjective questions of the patient related to the patient's overall pain level, the patient's mood, the patient's satisfaction with a particular stay in a hospital, the patient's satisfaction with a visit to an urgent care center, and the like. The clinical data and/or medical device data request module can also ask clinical questions such as the patient's physical areas of swelling, or direct the patient to perform a certain clinical test or task such as taking one's weight, blood pressure, pulse, blood sugar, and the like. The medical device data request module can ask for the patient to input medical device data and/or receive the medical device data automatically.

As stated above, the clinical data and/or medical device data request module can have a health or clinical data baseline for the patient, i.e. a series of values for the patient's bodily functions such as blood pressure, weight, pulse, etc., and data input by the patient can be compared to the baseline. In addition the system can provide a certified decision and/or protocol in response to clinical data input by the patient that is processed through an algorithm, a decision tree, and the like. It is appreciated that the system can also include the availability for a health care provider to review, agree, and/or change the certified decision and/or protocol, all decisions and data points being recorded in a secure database.

The certified algorithm/decision tree can be for one or more diseases or co-morbidities, illustratively including chronic obstructive pulmonary disease (COPD), heart failure (HF/CHF), asthma, diabetes, obesity, hypertension, arthritis, chronic pain, clinical depression, sleep apnea, coronary heart disease, and the like. The certified algorithm/decision tree can also be for one or more medical devices, illustratively including anesthesiology devices; cardiovascular devices; clinical chemistry and clinical toxicology devices; dental devices; ear, nose, and throat devices; gastroenterology and urology devices; general and plastic surgery devices; general hospital and personal use devices; hematology and pathology devices; immunology and microbiology devices; neurology devices; obstetric and gynecologic devices; ophthalmic devices; orthopedic devices; physical medical devices; and radiology devices.

Furthermore, the system can include validation for an end-to-end chain of custody with respect to information and/or actions provided, received and/or taken by the patient and/or clinician. For example, the validation for end-to-end chain of custody can include a visual and/or audible signal for one or more of the following: clinical and/or medical device data provided by the patient; review and/or analysis of the clinical and/or medical device data by one or more certified algorithms, decision trees, etc., provided by the system; production of a certified treatment or intervention protocol reviewed by the one or more certified algorithms, decision trees, etc.; review of the certified treatment or intervention protocol by a clinician; delivery of the certified treatment or intervention protocol to the patient; and action taken by the patient in accordance with the certified treatment or intervention protocol. The system can also include decisions and/or protocols related to an inaction taken by the patient, for example sending of a message to the patient's caregiver, e.g. a son, a daughter, etc., phoning of the patient, phoning of 911, and the like if a patient does not execute a desired action, instruction, etc., provided by the clinician via the system.

Nonlimiting and illustrative examples of data input queries provided to the patient by the system include requests related to a patient's peak flow measurement value from a blow into a spirometer, pulse rate, body temperature, sputum, cough, wheeze, sore throat, nasal congestion, nausea, urination, shortness of breath, fatigue, swelling of joints, abdominal pain, and the like.

The system can have a clinical data and/or medical device data analysis module with the certified algorithm and/or decision tree and the clinical data and/or medical device data analysis module can be part of, or be in the form of, a paper-based manual system, a web-based assessment tool, clinical guidelines, health risk assessments, staffed clinician call-center, pharmaceutical protocol, best practice for a given disease, and the like. The clinical data and/or medical device data analysis module can also provide an indication of severity of the specified clinical illness as a function of the clinical data input by the patient. In addition, the clinical data and/or medical device data analysis module can compare the indication of severity to the health baseline of the patient and/or to a standard intervention protocol based on that specific level of severity, and then provide an assessment of the patient without the patient having to travel to a doctor's office, urgent care center, hospital, etc.

The system can also be part of an accountable care organization (ACO) composed of physicians, hospitals, nursing homes, home health agencies, and other provider organizations responsible for the cost and quality of care provided to a given population of Medicare patients. In particular, the system affords for physicians and hospitals to collaborate to prevent readmissions to the hospitals, duplicate tests, and reduce other sources of unnecessary cost, and the like, such that health care costs can be reduced with an increase in overall quality of care.

The medical device modules can be used for or with a medical device approved by the Food and Drug Association (FDA), for example an FDA approved Class II medical device or an FDA approved Class III medical device.

The end-to-end chain of custody visual notification can also be included. Such an end-to-end chain of custody visual notification affords for showing a chain of custody for a given medical device data reporting event. For example, the end-to-end chain of custody visual notification can show a completed step in a Pending Initial Data Review-Treatment Recommended-Treatment Reviewed and Approved-Approved Treatment Sent to Patient-Patient Acknowledges Receipt chain of custody.

A notification module can also be included such that the system monitors the patients' activity and/or at least one medical device, and notifies a named party or parties that a specified event did or did not take place. Such a notification can occur in the form of an SMS/Text message, a phone call, a fax, an email and/or a page and thereby notify the named party or parties that the specified event did, or did not, take place indicating an action is required.

BRIEF DESCRIPTION OF THE DRAWINGS

FIG. 4 is an illustrative example of a patient entry screen for an HF & COPD application according to an embodiment of the present invention;

FIG. 5 is an illustrative example of a screen for a patient to input subjective data related to breathlessness according to an embodiment of the present invention;

FIG. 6 is an illustrative example of a screen for a patient to input subjective data related to a quantity of sputum from the patient according to an embodiment of the present invention;

FIG. 7 is an illustrative example of a screen for a patient to input subjective data related to a color of sputum from the patient according to an embodiment of the present invention;

FIG. 16 is an illustrative example of screen showing a prior submission summary of clinical data input to an outside third party and the interventional results from those submissions, including the level of severity during the past submissions;

FIG. 17 is an illustrative example of screen for a clinician dashboard showing a summary of patient input data and level of severity for one or more patients;

Figure 18:
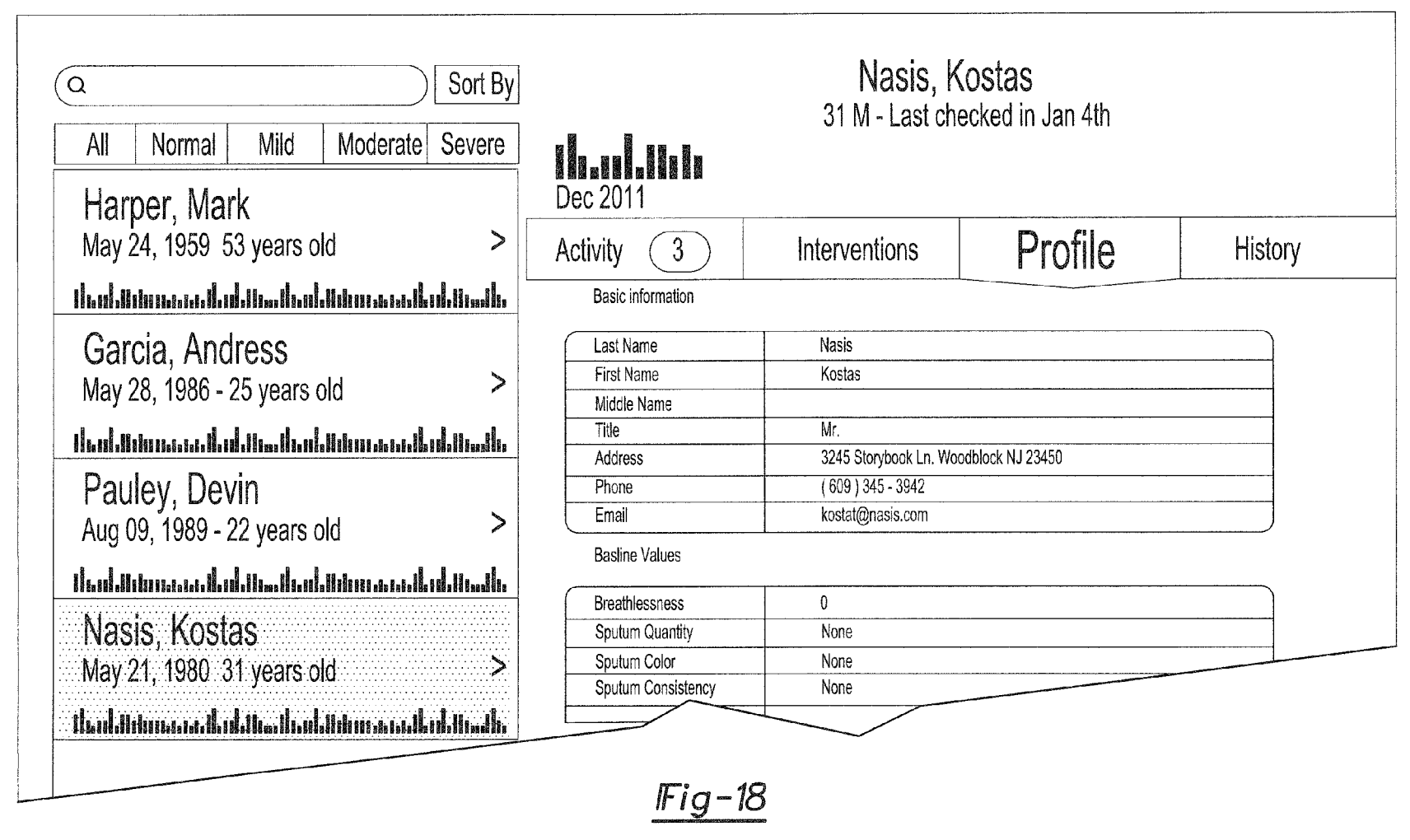

FIG. 18 is an illustrative example of screen for a clinician dashboard showing a patient baseline profile;

FIG. 19 is an illustrative example of screen for a clinician dashboard showing intervention protocol and chain of custody information;

FIG. 30 is an illustrative example of a screen for a patient to input subjective data related to the patient's overall personal experience with the IRPMM system; and is one of the 33 ACO metrics according to an embodiment of the present invention;

FIGS. 31 to 35 are illustrative examples of dynamic screens generated based on an answer provided to a screen illustrated in FIG. 26 with questions refining previously asked generic questions such as: Is your breathing worse at rest? (FIG. 31); If not, do you sleep well lying down? (FIG. 32); If yes, is it also worse during activity? (FIG. 33); If not, do you sleep well with additional pillows? (FIG. 34); If not, do you sleep well with sitting up in a chair? (FIG. 35);

DETAILED DESCRIPTION OF THE PRESENT INVENTION

A system for improving disease management for a patient is provided. As such, the system has use as a healthcare product.

The system can include a portable wireless device or a web-enabled connected device used by a patient to request clinical data from the patient and then provide clinical data to be reviewed or analyzed with a certified algorithm and/or decision tree. The certified algorithm and/or decision tree can then provide a summary of the data, indication of severity, "smart" or certified decision or intervention protocol to a clinician, e.g., nurse, doctor, and the like. For the purposes of the instant disclosure, the term "certified" refers to "physician approved," for example a physician approved algorithm, decision tree, decision, intervention protocol and the like.

In addition to the above, the system with the certified algorithm and/or decision tree can provide the summary of the data, indication of severity, "smart" decision or intervention protocol to the nurse, doctor, and the like within a short time frame, e.g. within 5 minutes from the data being provided by the patient. The certified decision and/or protocol can be agreed to and accepted or changed by an individual, e.g. a doctor, which can then be forwarded or sent back to the patient.

Upon receiving the decision and/or protocol, the patient is naturally instructed to execute the decision and/or protocol and the system provides a chain of custody to alert a clinician that the decision and/or protocol has been executed—an action, or in the alternative, has not been executed (an inaction) and alert a care giver, e.g. the assisted living home nurse, the son/daughter, or the like that the patient has not responded and may need help, etc. and needs to be contacted. In this manner, the use of the inventive system allows for a clinician, such as a nurse, to monitor a large number of patients, e.g. 250 patients, and thereby provide an improved disease management system as opposed to the average of 20-25 patients per day per clinician and thereby leaving a large part of the chronically ill patients unmonitored and unaccounted for and being one of the largest reasons for hospital re-admissions and escalating costs for the U.S. Healthcare System.

Additionally many hospital re-admissions are the direct result of not following the discharge notes or not reacting timely to changes in the patient's condition. Therefore, an improved interactive remote disease monitoring system that can automatically suggest one or more treatment intervention protocols, alert a health care provider of a potential problem with a patient's health and the like would be desirable. The system is implemented to create a more personal patient-physician relationship for the Care Coordination Team while encouraging self-management and individual responsibility, thereby leading to mutual accountability, and in the end, saving many lives.

Figure 1:
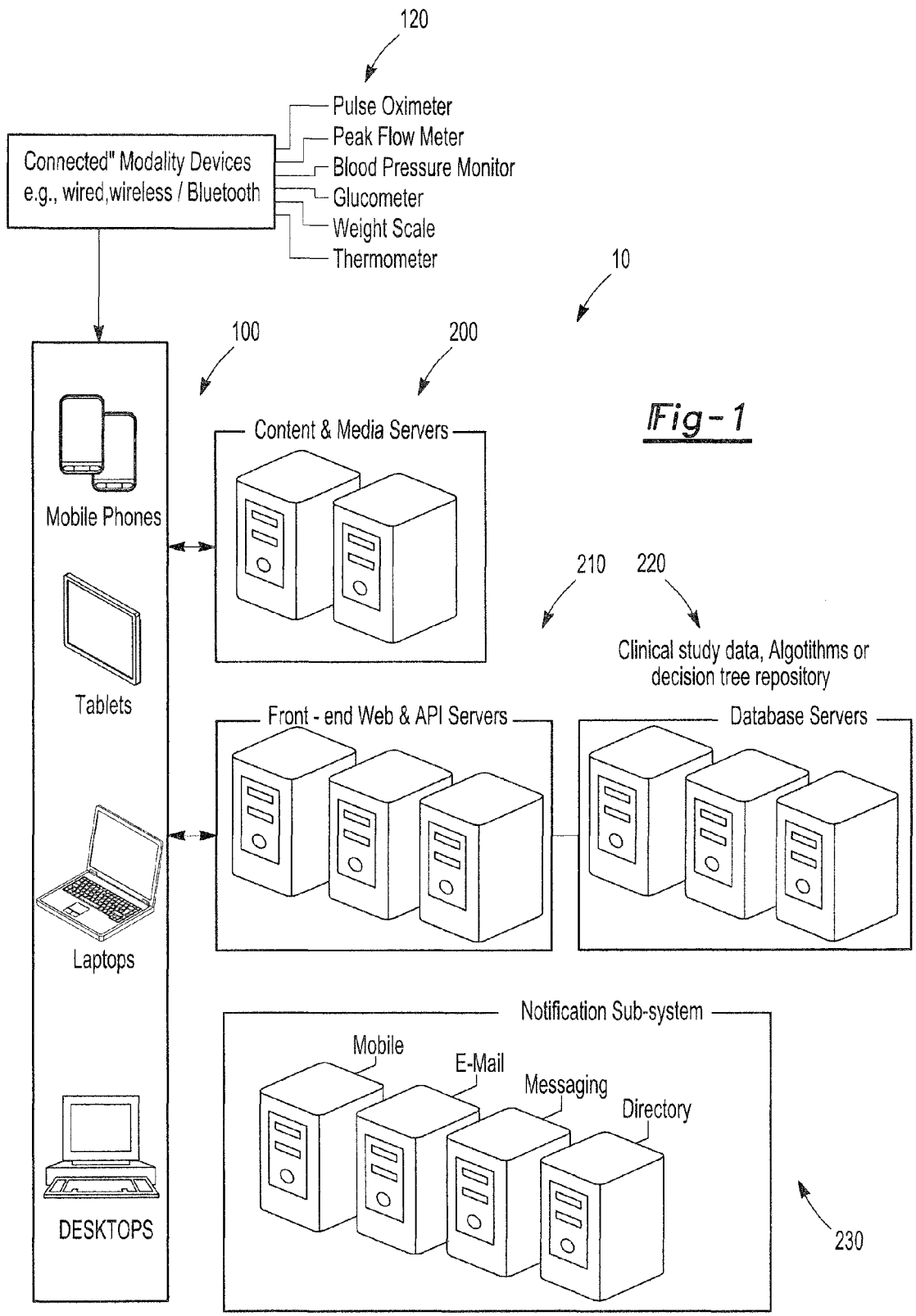
FIG. 1 is a schematic illustration of a system for improving disease management for a patient according to an embodiment of the present invention.

The portable wireless device can have an electronic control unit, memory, and an interactive remote patient-monitoring module (IRPMM) for at least one disease. It is appreciated that the portable wireless device can transmit and receive information to and/or from an outside third party or an in-house data center utilizing the IRPMM decision modules and framework as illustrated in FIG. 1. In addition, the IRPMM can have a clinical data request module that is operable to request and receive clinical data input from the patient related to the at least one disease and a clinical data supply module operable to receive clinical information from the outside third party and provide the clinical information to the patient. The clinical information can be an instruction, decision, treatment, intervention protocol or overall wellness information, and the like related to the at least one disease for the patient. It is appreciated that the clinical information can be a function of the clinical data input provided by the patient.

The system can also include certified algorithms and/or decision trees, results from a clinical study, a paper-based manual system, a web-based assessment tool, clinical guidelines, health risk assessments, staffed clinician call-center, pharmaceutical protocol, best practice for a given disease, and the like which can be used for providing a certified decision and/or interventional protocol as a function of the clinical data input by the patient. In this manner, an intelligent and dynamic "smart" system affords for providing a suggested method or step of treatment to be reviewed by an individual clinician or group care coordination team, e.g. a doctor. In addition, the system affords for a single individual, e.g. a nurse, to monitor up to 250 patients having one or more diseases on a periodic/regular basis. Stated differently, with the system requesting and receiving clinical data from the patient, and then processing the data and providing an indication of severity, recommended protocol, etc., to a clinician before or without any time required by the clinician, a vast improvement in healthcare efficiency can be provided and a decreased re-admission rate therefore occurs. The system also affords care to the entire population of chronically ill patients within a Healthcare System; rather than a select number that is limited by the current manual methods accomplishing patient care by speeding up the process and adding a level of mutual accountability that otherwise did not exist.

The system can also include a validation of an end-to-end chain of custody that ensures or gives notice that a patient has, or has not, taken prescribed and/or desired interventional actions provided by the doctor and/or nurse via the portable IRPMM wireless device. For example and for illustrative purposes only, a notice can be provided when a patient provides clinical and subjective data to a clinician, another notice provided when the data provided by the patient has been analyzed and a treatment or interventional protocol has been recommended by the system, the treatment has been reviewed and approved, the approved treatment has been sent to the patient and the patient has acknowledged receiving the approved treatment. In addition, if the patient does not acknowledge receiving of the treatment and/or affirmation that the treatment has been executed, an incident of inaction can be generated and the system can send a SMS/Text message, a fax, an email, a page or place a phone call, to notify the named party or parties, e.g., caregiver of the patient such as a relative, a home care provider, and the like that the specified event did, or did not, take place and indicating what specific action is required based on the level of severity and the intervention decision.

Turning now to FIG. 1, a schematic diagram of a system 10 according to an embodiment of the present invention is shown. A wired or wireless device 100 such as a mobile phone, a portable tablet, a laptop computer, a desktop computer, and the like can be included in the system, the device 100 having connected modality devices that can send and/or receive information using a wireless connection, a Bluetooth connection, a wired connection, etc. The device 100 can have an electronic control unit, memory, and an interactive remote patient-monitoring module (IRPMM) for at least one disease, the IRPMM operable to request and receive subjective and clinical data from a patient.

The IRPMM can include connected (Physical or wireless/Bluetooth) or manually entered data from clinical data modules 120, e.g. a module for taking/measuring or accepting data from a pulse oximeter, a peak flow meter, a blood pressure monitor, a glucometer, a weight scale, a thermometer, and the like. It is appreciated that the IRPMM is not limited to such individual data requests as stated above, and can include additional specific data requests that would be asked of a patient during a visit to a doctor's office, a visit to an urgent care center, a visit to an emergency room, and the like. For example, data requests can include general subjective questions such as "How are you feeling?", "Do you feel depressed?", "What is the overall level of your pain?", and the like. Questions such as "What is your overall satisfaction level with your hospital visit?", "What was your impression of the hospital staff?", and the like can also be provided to a patient to gather data on such issues, aspects, etc. of a health care event or ACO mandates and guidelines.

The IRPMM can also ask questions such as "Are you still smoking?", and if answered in the affirmative, the system can provide information, programs, etc. on how to quit smoking, the dangers of smoking, etc. Furthermore, the system can provide advertising and education for health-related matters such as quitting smoking, losing weight, exercise, etc. It is appreciated that such information can be contained on content and media servers 200 illustratively shown in FIG. 1, which can be in wireless, wired or manually entered communication with one or more of the devices 100.

Front-end web and application programming interface (API) servers 210 which may or may not be in communication with database servers 220 that have clinical study data, algorithms, decision trees, and the like can also be part of the system 10. It is appreciated that the database servers 220 can have proprietary information, algorithms, decision trees, and the like developed by a particular Healthcare System, Hospital, Doctor, etc., and/or publicly available/Public Domain clinical study data, algorithms, decision trees, and the like that can be used to make expert decisions on clinical data provided by one or more patients with one or more chronic illnesses or co-morbidities. It is also appreciated that the database servers 220 can be connected to a Healthcare or Ambulatory System's existing legacy solutions, e.g., Electronic Medical/Health Records (EMR/EHR), Enterprise Practice Management Systems (ePMS) and Health Information Exchange (HIE) and the like via various legacy connections such as HL7, and the like to share data among various systems, or the IRPMM can not connect to any other system, acting as a HIPAA-compliant stand alone solution. The system can further include a notification sub-system 230 that can notify the patient, the doctor, nurses, relatives, etc. using email, text messaging, mobile wireless communication, and the like based on the results of the chain of custody and its action/inaction events.

It is appreciated that by interconnecting the various components/appropriate tools of the system 10 with clinical specialists for disease management and using the components/appropriate tools with or for a chronic illness populace, overall costs, e.g. hospital encumbrance, insurance expenses, etc., can be reduced. In addition, clinical specialists, e.g. nurses, physicians, etc., can function more efficiently and lives can be saved with unnecessary exacerbations and/or chronic illness episodes monitored and intervened ahead of time, allowing for shared accountability, and with a reduction of future complications associated with a particular disease reduced. By creating intelligent and measurable, real-time, data-driven health outcomes reduces hospital re-admissions, improves quality of life, allows for effective cost savings opportunities, provides better care coordination for nurse/clinician treatment teams, allows disease-specific self-monitoring and personalized care plans.

Illustrative chronic illnesses that the system 10 can be used to improve medical treatment for, but are not limited to, heart failure (CHF/HF), chronic obstructive pulmonary disease (COPD), asthma, diabetes, obesity, hypertension, arthritis, chronic pain, clinical depression, sleep apnea, coronary heart disease, and other prolonged conditions. For example and for illustrative purposes only, COPD is a leading cause of mortality and morbidity worldwide, affecting approximately 210 million people and leading to 3 million deaths annually. In the United States alone, COPD is the fourth leading cause of death and accounts for 15.4 million physician visits, 1.5 million emergency department visits, and 636,000 hospitalizations each year. Based on national survey data, the total economic burden of COPD in the United States in 2007 was calculated to be $46.2 billion. This calculated cost included $26.7 billion in direct health care expenditures of which $11.3 billion was for hospital care alone. In addition, the above data for COPD is expected to increase considerably as the population in the United States continues to age.

In addition to the above, patients with COPD experience exacerbations one to three times a year with treatment often requiring emergency room or hospitalization. It is appreciated that emergency room and/or hospitalization contributes substantially to the financial burden of the disease. In addition, depending on the population studied, an estimated 25-47% of patients with COPD are hospitalized and as many as 26% have emergency room visits (Re-Admissions) annually that can be substantially reduced by the inventive system 10. Finally, various observational studies have found that inpatient care accounts for 52-70% of the direct medical cost of COPD.

Given the above statistics, it is appreciated that the inventive system 10 disclosed herein can provide a vast improvement in care for such patients and a significant reduction in costs associated with caring for such patients. For example and for illustrative purposes only, the disease management system 10 and a method of using the system 10 can provide technology-based remote interactions between a patient and a clinician utilizing "connected" devices that allow patients to put their health data manually into a phone-connected or wireless device having an interactive remote patient monitoring module (IRPMM) specific in nature to a particular illness, a web portal or service, and the like. The manually entered health data can also include data from instruments such as a weight scale, a blood pressure cuff, a blood sugar monitor, and the like. The data can also be transferred to a web-based portal until a clinician has time to view the data.

The web-based portal can have publicly available and/or confidential certified algorithms, decision trees, and the like to analyze the health data, compare the health data to baseline data for a particular patient, etc. As mentioned above, the algorithm, decision tree, etc. can provide a summary and/or an overall indication of severity for the health data automatically or manually input by the patient and the summary and/or overall indication of severity can be reviewed by a clinician to determine or suggest an intervention protocol. In the alternative, the "smart" system can suggest an intervention protocol and the clinician can accept and/or modify the protocol before sending to the patient. It is appreciated that for some chronic illness patients' interventions can be performed on a periodic basis, for example a daily basis. As such, input of health data manually into a web portal, service, or wireless device can provide for daily check ups on the patient and review of the patient's data by a clinician in order to monitor and hopefully intervene unnecessary chronic illness episodes such as unnecessary exacerbations for COPD patients, thereby optimizing mutual accountability of health outcomes and increasing their results in a positive direction. In summary, the inventive system and method can deliver interventions to patients based on the utilization of various algorithms and/or decision trees that have been established and statistically validated either by an actual clinical trial study or by a specific health system, clinician's or physician's methodology for treating patients.

In some instances, a numbering or indication of severity system can be generated by a known set of subjective and data driven clinical patient questions that can be entered into the IRPMM which can generate one or more results determined by the patient specific baseline data and/or an overall indication of severity model. The baseline comparative results and/or indication of severity can be initially generated from a patient's response to a series of questions provided by the IRPMM to the patient and the baseline comparative results and/or indication of severity can be compared to a standard intervention protocol already established within a specific chronic illness. This comparison or matching of the baseline comparative results and/or indication of severity to an intervention protocol can be in an easy to use format that does not require intensive learning on the part of all users of the system. In fact, the system is naturally intuitive and the interventions become predictive over time.

After the generation of the baseline comparative results and/or indication of severity and possible comparison or matching to a standard intervention protocol, a suggested intervention or treatment protocol can be approved by one or more clinicians and sent back to a particular patient. As such, a new and useful system in the area of remote disease monitoring and management that uses artificial intelligence and/or expert analysis of health data input by a patient is provided. Such a system can also be utilized in other areas and markets similar or dissimilar to the healthcare industry.

Returning now to FIG. 1, the inventive system can utilize wireless tablet computers and smart phones connected via the Internet or implemented over the cloud, sometimes referred to as cloud computing. Such wireless tablet computers and smart phones are known to exist under the trademark names of Apple iPad, Apple iPhone, Android tablets, Android smart phones, Windows mobile tablets, Windows mobile smart phones, and other platforms that are conducive for easy use. It is appreciated that the system 10 can also be used on or with new technologies as they become available.

In one example of the system 10 and its use, an IRPMM on a smart phone allows a patient to manually enter clinically required or subjective data points, e.g. a value of a resultant peak flow measurement from a blow into a spirometer; how the patient feels in general on a day, such as their breathlessness; a patient's sputum quantity; and the like. Such data input can be based on a series of questions provided to the patient via the IRPMM and the answers to the questions can be converted to an indication of severity that is derived from a combination of the patient's answers and a matching of the answers to a severity of their illness with respect to baseline information that is taken into consideration for a specific chronic illness or comorbidity.

If a patient has more than one chronic illness, such as COPD and CHF, the IRPMM can include specific questions for the COPD chronic illness and another set of specific questions for CHF. The IRPMM can also process answers related to the COPD and the answers related to the CHF and provide a summary and/or associated indication of severity for each illness in order to determine appropriate intervention(s), and report the indication of severity and/or a suggested intervention protocol for a clinician's review, approval, modification, and the like. Naturally, once a clinician approves an intervention protocol, such protocol is sent and provided back to the patient.

Such protocols can be statistically valid trials or clinician experience-based indication of severity systems associated with a standard intervention protocol system that is accepted across the health care industry for a particular chronic illness specialty. For example, the global strategy for diagnosis, management, and prevention of COPD generated by the Global Initiative for Chronic Obstructive Lung Disease (GOLD) can be loaded into the inventive system and can be used to compare the data, indication of severity, etc. obtained from the clinical data of a particular patient to a baseline for the particular patient and suggest an intervention protocol.

An accepted or altered intervention protocol is provided back to the patient and allows real-time remote disease monitoring that effectively allows a clinician to communicate an intervention to a patient prior to the patient unnecessarily traveling back to a hospital and incurring a heavy financial burden on the hospital, insurer, patient, etc. The system can notify the patient via the patient's smart phone or device that a message has been received from the clinician, the smart phone or device notifying the patient by a ring, vibration, and the like. The patient can then reopen the IRPMM and accept the resultant intervention protocol by acknowledging the acceptance thereof and also possibly acknowledging that the result of the protocol has been successful or in the alternative is not successful, and the patient is calling 911 and/or is traveling to a doctor's office, an emergency room, etc. It is appreciated that the smart phone or device can have HIPAA-compliant software loaded thereon with regular updates provided as known to those skilled in the art.

For illustrative purposes only, and in no way limiting the scope of the invention, an example will be provided below in which the system 10 and its use are described with respect to a smart phone used by a patient and a smart tablet used by a clinician in the treatment of one or more patients with COPD.

EXAMPLE

Figure 2:
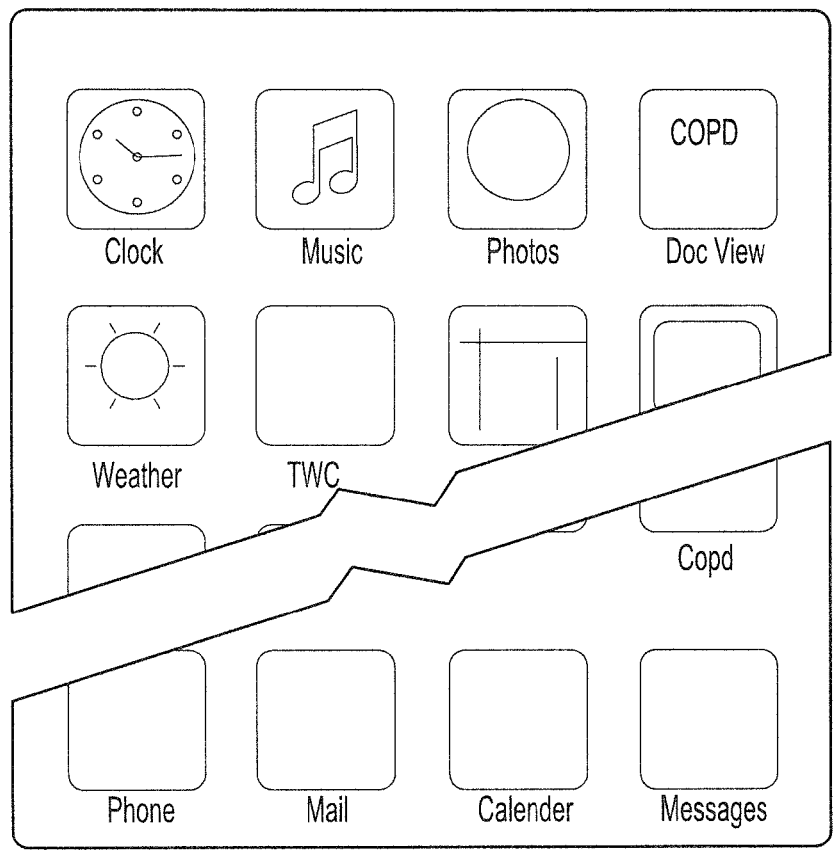
FIG. 2 is an illustrative example of a screen of a portable wireless device having a Congestive Heart Failure (CHF or HF) and a chronic obstructive pulmonary disease (COPD) application according to an embodiment of the present invention.
Figure 3:
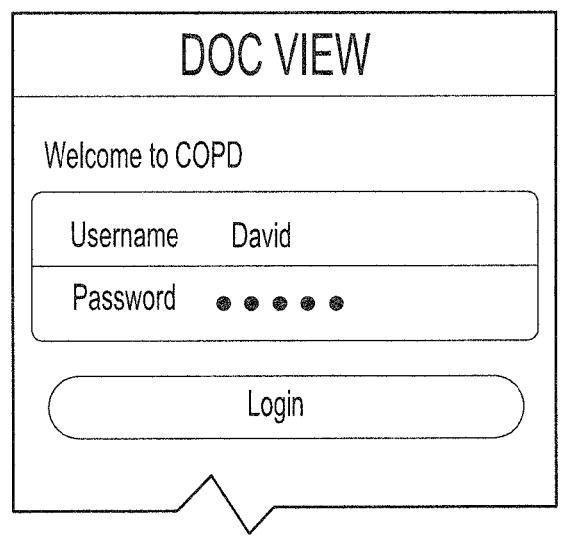
FIG. 3 is an illustrative example of a login screen for an HF & COPD application according to an embodiment of the present invention.

Referring now to FIG. 2, a schematic diagram of a home screen for a smart phone is shown with illustrative examples of applications such as a clock, weather, and the like. It is appreciated that one of the applications can be representative of the inventive system disclosed herein, for example an application related to COPD using an application format hereafter referred to as "DOC VIEW". FIG. 3 illustrates a schematic screenshot of a login screen in which a COPD IRPMM application is provided, the login screen having an area for input of a user name and a password as is known to those skilled in the art. As such, it is appreciated that a patient can select the DOC VIEW application from FIG. 2 and input his or her user name and password in FIG. 3 to enter the DOC VIEW application in order to provide clinical data related to COPD.

After entering the user name and password, FIG. 4 illustrates a schematic screenshot of an entry screen in which selections for checking in, sending a message, reviewing recent activity, and the like are provided. In addition, FIG. 5 provides a schematic screenshot for a breathlessness screen that can be part of clinical data input requested from a patient. As shown in FIG. 5, the patient can be requested to select a particular level of breathlessness ranging from 0 (none) to 10 (extremely) and thereby provide a subjective data input for future analysis. The patient can also select the previous screen or the next screen provided by the buttons shown at the bottom of FIG. 5, which naturally allows the patient to navigate through the COPD application.

Figure 8:
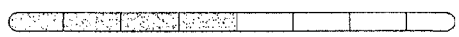
FIG. 8 is an illustrative example of a screen for a patient to input subjective data related to a consistency of sputum from the patient according to an embodiment of the present invention.
Figure 9:
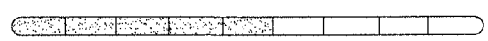
FIG. 9 is an illustrative example of a screen requesting clinical data input from a patient related to a peak flow measurement value from a blow into a spirometer.

For example and for illustrative purposes only, by selecting the Next screen in FIG. 5, the DOC VIEW application can request a sputum quantity value/datum from the patient as shown in FIG. 6. A series of selections can be provided as shown in FIG. 6 such as the sputum quantity being none, less than 1 tablespoon, greater than or equal to 1 tablespoon, greater than ¼ cup, and the like. It is appreciated that these exact selections can be modified according to a particular IRPMM, a doctor's changes to the questions, and the like. After selecting one of the quantity levels in FIG. 6, the patient can select/touch the Next button at the bottom of the screen which then affords for the application to request an input for sputum color as shown in FIG. 7. After the patient selects one of the sputum colors, he/she can select/touch the Next button and be taken to a screen requesting an input for sputum consistency as illustratively shown in FIG. 8. As shown in FIG. 8, the patient has illustratively selected Thin, and can then select Next which can take the DOC VIEW application to the screen shown in FIG. 9 which provides a plurality of data choices related to blowing into a spirometer with a selection available for a first attempt, a second attempt, a third attempt, and the like.

Figure 10:
FIG. 10 is an illustrative example of a screen requesting clinical data input from a patient related to the patient's body temperature.

The COPD DOC VIEW application can also include a request for body temperature data as illustrated in FIG. 10. In particular, the screenshot shown in FIG. 10 illustrates asking a patient if their temperature is over 100°. In the alternative, the application can ask for a specific value to be input by the patient.

Figure 11:
FIG. 11 is an illustrative example of a screen requesting multiple clinical data inputs from a patient related to cough, wheeze, sore throat & nasal congestion.

Referring now to FIG. 11, the DOC VIEW application can provide questions to the patient as to whether or not he/she have been coughing, wheezing, has a sore throat, nasal congestion, and the like. The system can take such answers for future analysis, or in the alternative, based on answers provided on the screen represented by FIG. 11, ask more detailed questions such as how persistent a cough has been, how severe wheezing has been, how severe the sore throat is, etc. As such, the application and thus the system 10 can be tailored for a specific disease, patient and the like by asking specific questions, requesting particular data input, etc.

Figure 12:
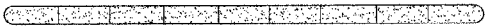
FIG. 12 is an illustrative example of a screen providing a summary of subjective & clinical data input by a patient.
Figure 13:
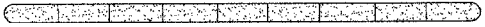
FIG. 13 is an illustrative example of a screen providing a questionnaire to a patient to confirm or not confirm whether or not a summary of clinical data input by the patient is correct and therefore allowing the patient the option to make a change, if required.
Figure 14:
FIG. 14 is an illustrative example of a screen showing a report has been submitted to an outside third party and providing the patient an opportunity to send a message or to make a phone call.

FIG. 12 illustrates a summary of the data input by the patient, such a screen allowing the patient to review the data he or she has input into the system. Such a screen also affords for the patient to change and/or edit the data if he or she sees that a mistake has been made. FIG. 13 affords for the patient to confirm whether or not the summary information is correct and if the information is correct, submit the data to a clinician as illustrated in FIG. 14. It is appreciated that if the patient selects No, that the summary is not correct, that the system allows for the patient to go back and edit, modify, etc., data that was input. FIG. 14 also illustrates additional options such as texting a clinician, calling a Nurse, 911, etc., can be provided as part of the DOC VIEW application.

Figure 15:
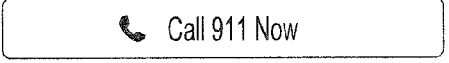
FIG. 15 is an illustrative example of a screen allowing a patient to review prior submissions of clinical data input to an outside third party and the interventional results from those submissions, including the level of severity during the past submissions.

FIG. 15, similar to FIG. 4, allows a patient to review recent activity such as a response received in the past. For example, FIG. 16 shows a prior submission summary screen in which a summary indication of severity bar graph report is provided at the top of the screen and allows a patient to monitor their daily health level and anticipate if an intervention protocol will be suggested by the clinician. In addition, such an indication of severity, both past and present, can provide real-time feedback to the patient with respect to the disease and their health and incorporate predictive modeling for the clinicians' use.

Figure 17:
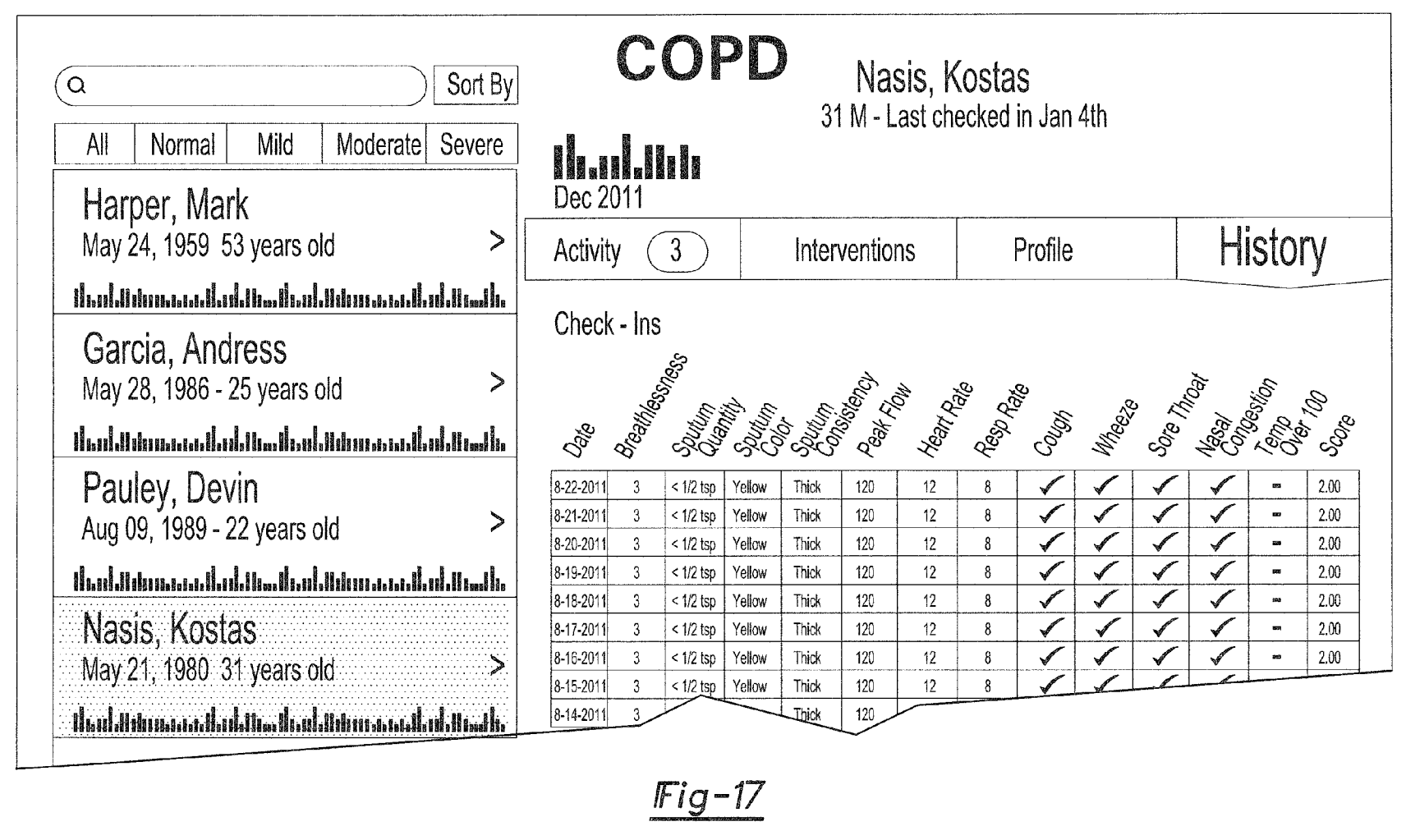

The data, summary, report, and the like can be wirelessly transmitted to the web-based portal or servers 210 which can be accessed by a clinician and analyzed and/or compared by or to a clinical study, an algorithm, decision tree, etc., made available on the database servers 220. For example, FIG. 17 shows a screenshot of, e.g. a smart tablet, which has a series of patient records and data for the COPD disease. The system affords options on how to sort (Sort By button) through the patients and/or the data, for example selecting All of the patients, only patients having a Normal level of wellness with respect to COPD, a Mild level, a Moderate level, and/or a Severe level of the indication of severity. As illustratively shown in FIG. 17, a patient having an example name of Kostas Nasis has been selected and History providing a summary of data for dates ranging from Aug. 14, 2011 to Aug. 22, 2011 is shown with values for breathlessness, sputum quantity, and the like viewable by a clinician. In addition, an overall indicator is shown utilizing various colors to indicate severity classifications which can be provided by certified algorithms, decision trees, and the like which provide expert decisions for review by a clinician. Furthermore, graphical results can illustrate, for example by the bar graph with the label of December 2011 underneath, the name for a given time period.

Figure 19:
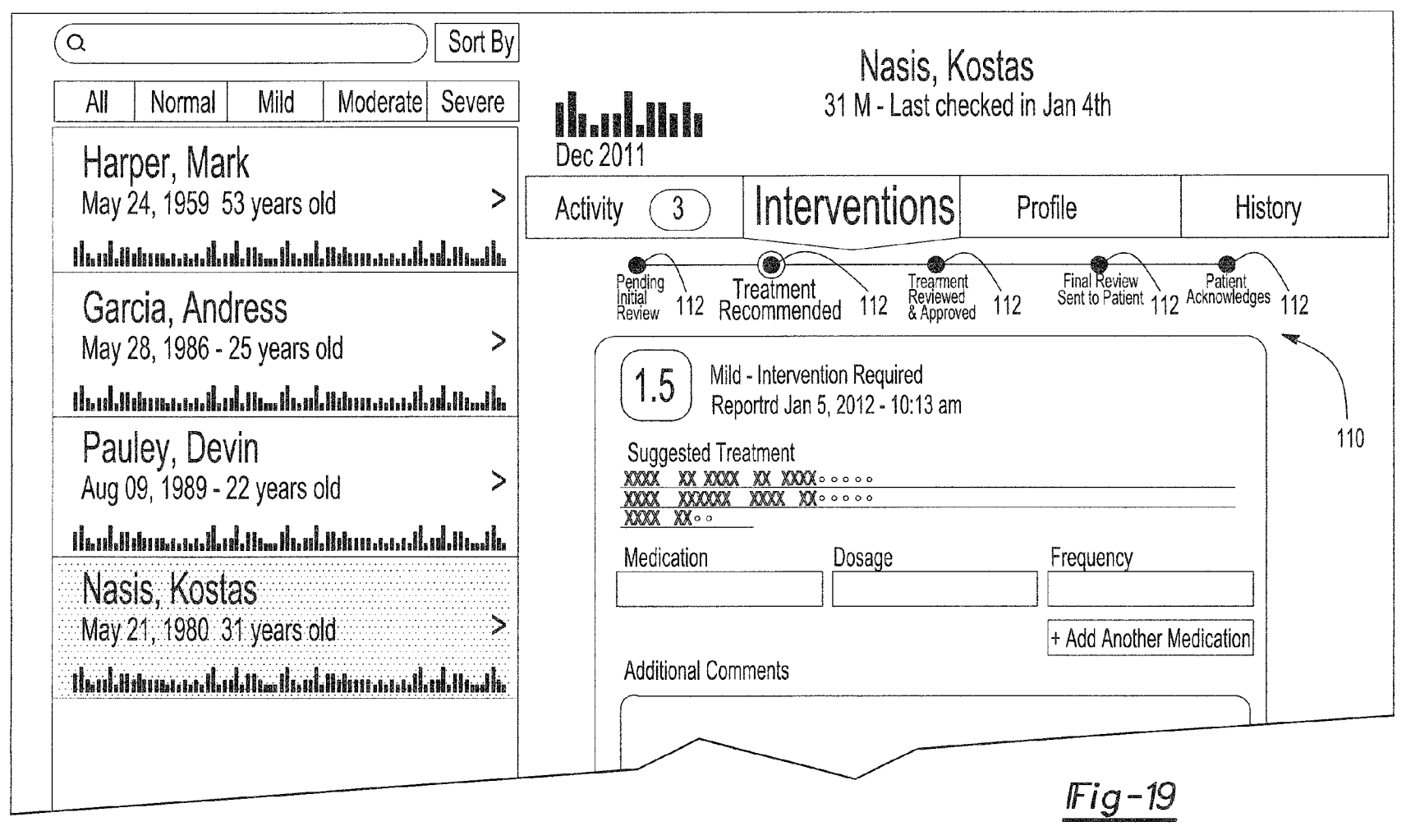

Referring now to 18, a baseline profile screen for the patient Kostas Nasis allows the entry of the patient's name, address, and the like which are then provided in a time efficient and convenient manner to the clinician. Finally, FIG. 19 provides the interventions suggested or provided to the patient along with a chain of custody history 110 provided by the dots 112 shown with text underneath. In particular, FIG. 19 illustratively shows dots or lighted circles that correspond to Pending Initial Review of the data, Treatment Recommended, Treatment Reviewed and Approved, Final Review Sent to Patient, and finally Patient Acknowledges receipt. In this manner, the system can show and record end-to-end custody chains for a particular patient on a periodic basis. Also shown in FIG. 19 are locations for the clinician to provide suggested treatment in the form of instructions, medication with dosage, frequency, and the like, and additional comments. It is appreciated that the data can be stored within one or more servers illustrated in FIG. 1.

The system can also take proactive actions with respect to calling in prescriptions for a particular patient, calling 911 for a patient, setting up a visit with an ambulatory physician or specialist and the like. For example, if a patient's smart phone has a GPS unit and the patient has selected or requested that the DOC VIEW system have access to GPS data from the smart phone, the DOC VIEW system can ask the patient if they would like a prescribed medication to be filled at a particular pharmacy that is in the proximity of the patient's smart phone. For example, if the patient is traveling, the DOC VIEW system can automatically determine this fact and ask the patient if the medication should be called in at the patient's regular pharmacy or a pharmacy that is located nearer to the present location of the patient.

Figure 20:
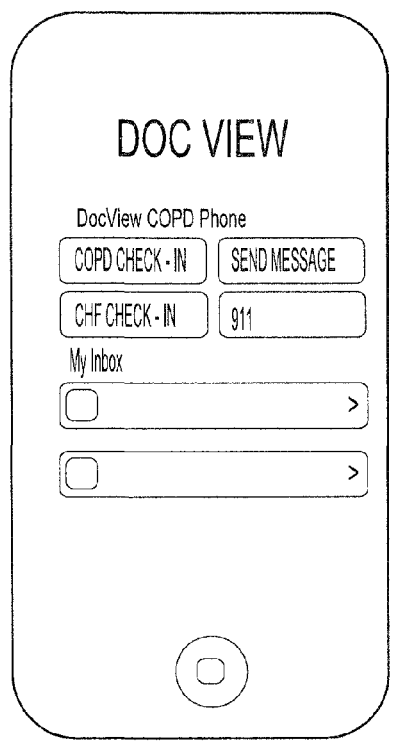
FIG. 20 is an illustrative example of a patient entry screen for an HF & COPD application according to an embodiment of the present invention.
Figure 21:
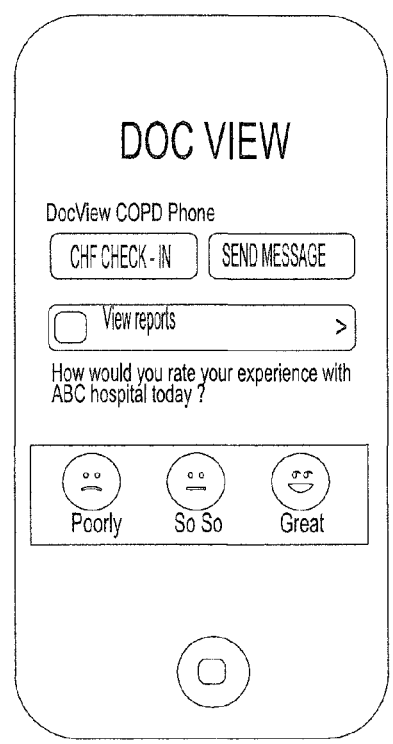
FIG. 21 is an illustrative example of a screen for a patient to input subjective data related to their overall personal experience with the medical system utilizing one of 33 ACO metrics according to an embodiment of the present invention.
Figure 22:
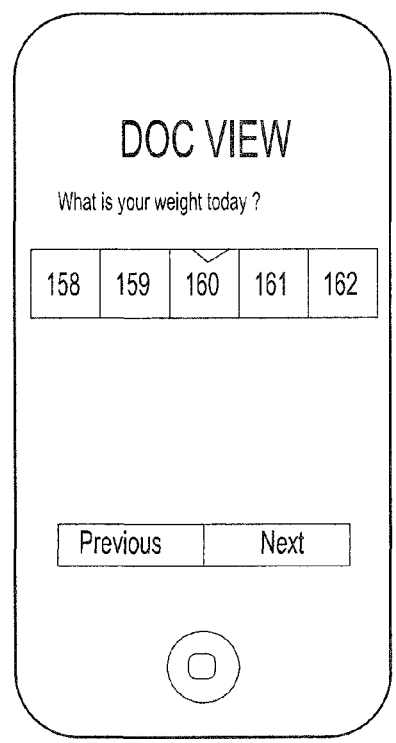
FIG. 22 is an illustrative example of a screen for a patient to input clinical data related to weight according to an embodiment of the present invention.
Figure 23:
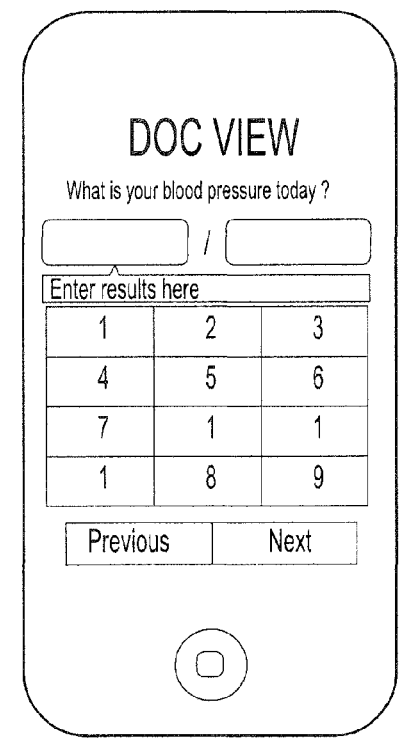
FIG. 23 is an illustrative example of a screen for a patient to input clinical data related to blood pressure according to an embodiment of the present invention.
Figure 24:
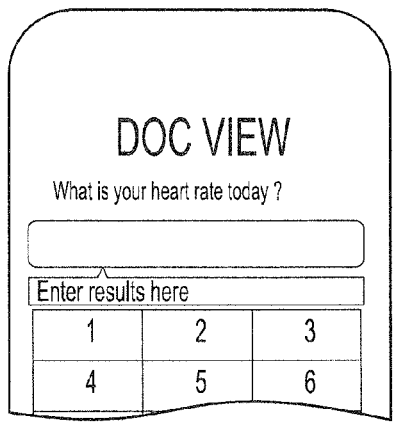
FIG. 24 is an illustrative example of a screen for a patient to input clinical data related to heart rate according to an embodiment of the present invention.
Figure 25:
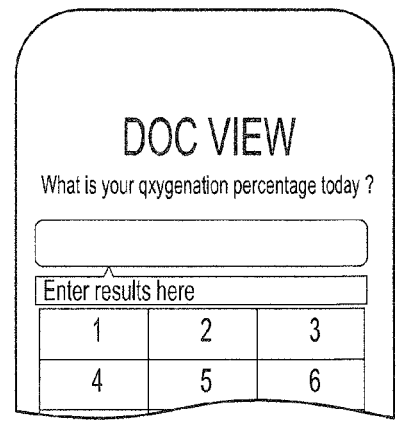
FIG. 25 is an illustrative example of a screen for a patient to input clinical data related to oxygenation percentage according to an embodiment of the present invention.

Although the example above is provided for COPD, it is appreciated that the system 10 and DOC VIEW application can have IRPMM modules for different diseases such as those listed above. For example FIG. 20 provides an illustrative example of a patient entry screen for an HF & COPD application that allows a patient to enter a COPD or CHF check-in, send a message and/or call 911 is shown. The system can also have a screen for a patient to input subjective data related to their overall personal experience with the medical system utilizing one of 33 ACO metrics as shown in FIG. 21. Upon entering the COPD and/or CHF application/module, the system can provide a screen for a patient to input clinical data related to weight as shown in FIG. 22. In addition, FIG. 23 provides an illustrative example of a screen for a patient to input clinical data related to blood pressure according; FIG. 24 illustrates a screen for a patient to input clinical data related to heart rate; FIG. 25 illustrates a screen for a patient to input clinical data related to oxygenation percentage; and FIG. 26 a screen for a patient to input clinical data related to breathing, all of which can be used to create decision trees illustrated in FIGS. 31 to 35 to be discussed below.

Figure 27:
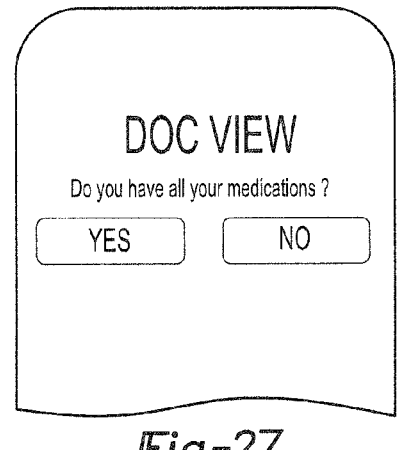
FIG. 27 is an illustrative example of a screen for a patient to input subjective data related to medication usage according to an embodiment of the present invention.
Figure 28:
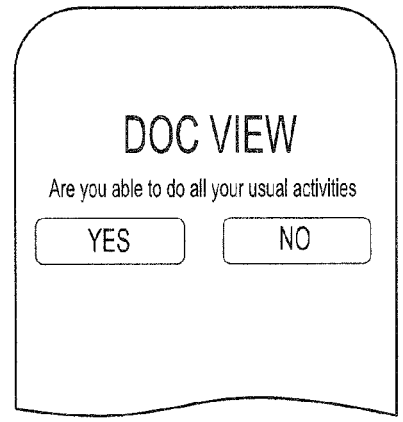
FIG. 28 is an illustrative example of a screen for a patient to input subjective data related to activity according to an embodiment of the present invention.
Figure 29:
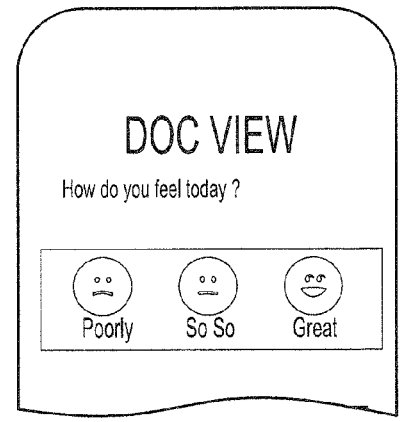
FIG. 29 is an illustrative example of a screen for a patient to input subjective data related to wellness according to an embodiment of the present invention.

FIG. 27 provides an illustrative example of a screen for a patient to input subjective data related to medication usage while FIG. 28 is an illustrative example of a screen for a patient to input subjective data related to daily activity. In addition, FIG. 29 provides a screen for a patient to input subjective data related to wellness and FIG. 30 illustrates a screen for a patient to input subjective data related to the patient's overall personal experience with the IRPMM system.

Figure 26:
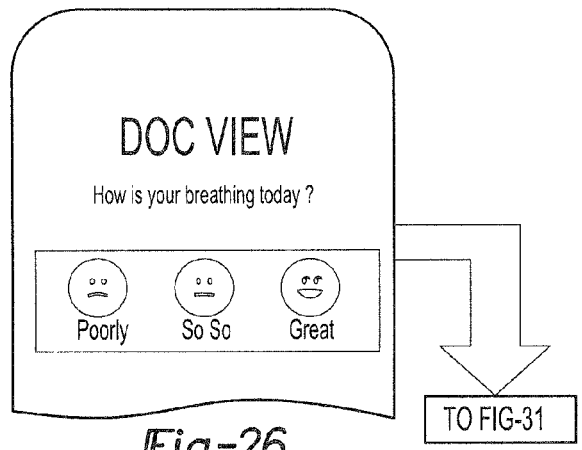
FIG. 26 is an illustrative example of a screen for a patient to input clinical data related to breathing used to create decision trees illustrated in FIGS. 31 to 35 according to an embodiment of the present invention.

Regarding FIGS. 31 to 35, illustrative examples of dynamic screens generated based on an answer provided to the screen shown in FIG. 26 provides with questions that refine previously asked generic questions such as: Is your breathing worse at rest? (FIG. 31); If not, do you sleep well lying down? (FIG. 32); If yes, is it also worse during activity? (FIG. 33); If not, do you sleep well with additional pillows? (FIG. 34); If not, do you sleep well with sitting up in a chair? (FIG. 35).

Figure 36:
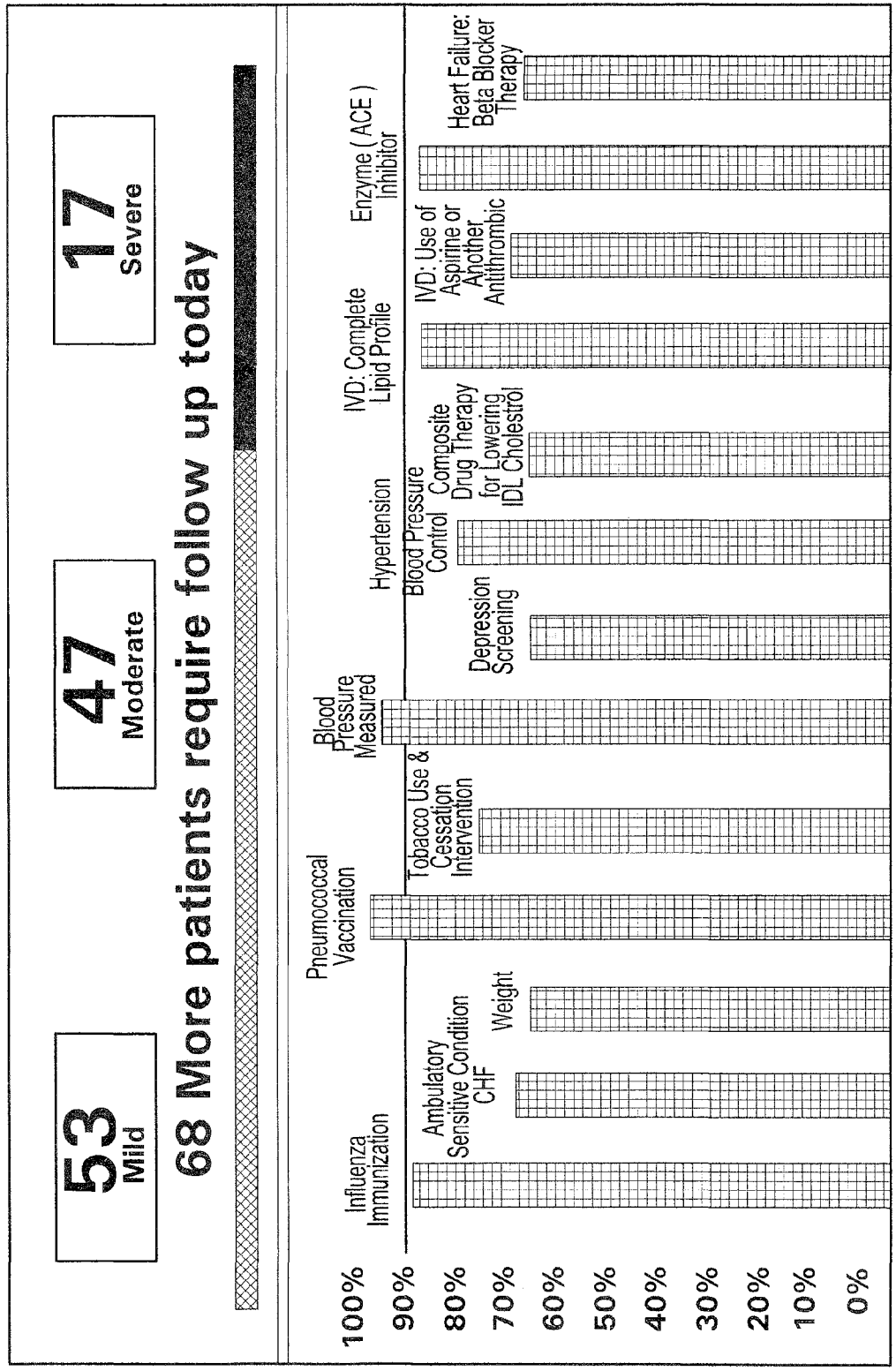
FIG. 36 is an illustrative example of a clinician reporting screen for a patient or a group of patients illustrating how many patients have been seen or reported their conditions and how many more patients need to be followed up with and how a Healthcare Institution, e.g., a hospital, is doing based on specific ACO Metric Guidelines given to the Healthcare Institution by the USA Medicare Office or other Government Entity monitoring the Healthcare Institution's ACO goals and is a subset of the 33 ACO metrics according to an embodiment of the present invention.

FIG. 36 provides an illustrative example of a clinician reporting screen for a patient or a group of patients illustrating how many patients have been seen or reported their conditions and how many more patients need to be followed up with and how a Healthcare Institution, e.g., a hospital is doing based on specific ACO Metric Guidelines given to the Healthcare Institution by the USA Medicare Office or other Government Entity monitoring the Healthcare Institution's ACO goals and is a subset of the 33 ACO metrics according to an embodiment of the present invention.

Figure 37:
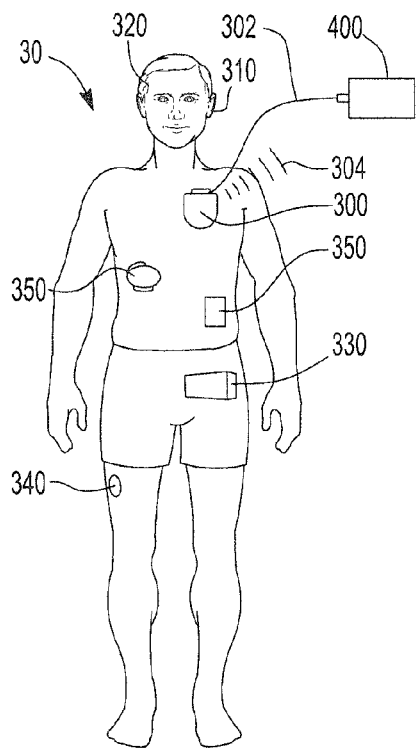
FIG. 37 is a schematic illustration of various medical devices that can be used by a patient.

Referring now to FIG. 37, a schematic illustration of a plurality of medical devices that can be used by a patient is shown generally at reference numeral 30. The patient and devices shown at 30 can include cardiac defibrillators and/or pacemakers 300, hearing implants (e.g., cochlear implants) 310, deep brain neurostimulators 320, insulin pumps 330, foot drop implants 340, gastric stimulators 350, and the like. In addition, non-implantable medical devices 350, i.e. medical devices that are worn by the patient but not necessarily implanted therewithin, can also be included. For each medical device, a download device 100 can be used to obtain data from the device. The download of the data can occur through a wired connection 302 or wirelessly as illustrated by electromagnetic waves 304.

In some instances, medical device data is downloaded to the download device 100 before being transferred to one or more connected modality devices discussed in FIG. 1. In the alternative, data from the medical devices can be transferred directly to one or more connected modality devices 100 discussed in FIG. 1.

Any medical device known to those skilled in the art can be used with the instant invention. For example, and in addition to the medical devices discussed above with respect to FIG. 37, devices such as electrocardiograph meters, heart rate meters, heart beat meters, oxygen saturation meters, blood sugar level meters, pedometers, devices to measure activity levels, thermometers, weight scales, blood pressure gauges, and the like are included.

As known to those skilled in the art, a medical device has a definition per the Federal Food, Drug, and Cosmetic Act (FD&C), United States Code 201(h). In addition, the FDA has three different classes of medical devices. Class 1 medical devices are deemed to have a minimal potential risk of causing harm and include examples such as tongue depressors, gloves, bedpans, handheld surgical instruments, etc. Class 2 devices are deemed to have a higher potential to cause harm and require both general and special controls with respect to special labeling, mandatory performance standards, and post-market surveillance. Such devices are typically nonimplanted; however, some are partially invasive. Such devices include x-ray machines, wheelchairs, infusion pumps, and surgical needles. Class 3 devices are deemed to pose a more significant potential risk to a patient and often because they are more invasive. Such devices require general controls and pre-market approval that includes scientific review to ensure a particular device's safety and effectiveness. Class 3 devices include heart valves, orthopedic prosthetic devices, cardiac pacemakers, etc.

In addition to the three classes of medical devices, the FDA classifies a device based on a medical panel/specialty to which it belongs. There are sixteen medical panels that include anesthesiology devices; cardiovascular devices; clinical chemistry and clinical toxicology devices; dental devices; ear, nose, and throat devices; gastroenterology and urology devices; general and plastic surgery devices; general hospital and personal use devices; hematology and pathology devices; immunology and microbiology devices; neurology devices; obstetric and gynecologic devices; ophthalmic devices; orthopedic devices; physical medical devices; and radiology devices.

Examples of anesthesiology devices include carbon dioxide gas analyzers, indwelling blood oxygen partial pressure analyzers, apnea monitors, and ventilators. Examples of cardiovascular devices include implantable pacemakers, implantable defibrillators, prosthetic heart valves, ventricular bypass (assist) devices, and intra-aortic balloon pumps. Clinical chemistry and clinical toxicology devices include glucose measurement devices, sodium and other electrolyte measurement devices, and various specific toxicology test kits. It is appreciated that other medical devices within the FDA medical device categories can be used and included within one or more embodiments of the present invention.

Figure 38:
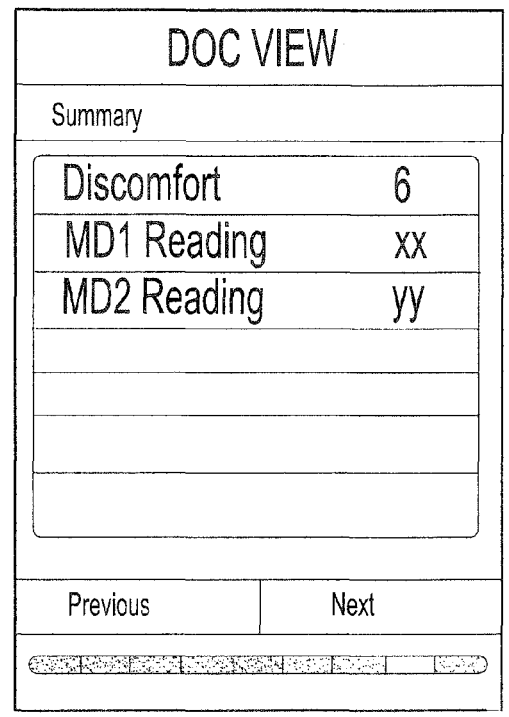
FIG. 38 is an illustrative example of a screen of a portable wireless device providing a summary of subjective input by a patient and data from at least one medical device.

Referring now to FIG. 38, an illustrative example of a screen of a portable wireless device having a medical device application is shown. As discussed previously with respect to FIGS. 1-36, FIG. 38 illustrates a summary of data input by the patient and readings for a first medical device (MD1) and a second medical device (MD2). It is appreciated that the screen can show the actual name of a medical device instead of the MD1 and/or MD2 label shown. For example and for illustrative purposes only, the screen could show a defibrillator reading with a value corresponding to an implanted defibrillator as known to those skilled in the art instead of the MD1 reading shown in the figure. Stated differently, the MD1 reading xx and MD2 reading yy are shown for illustrative purposes only in order to provide an example view of an embodiment of the present invention.

Figure 39:
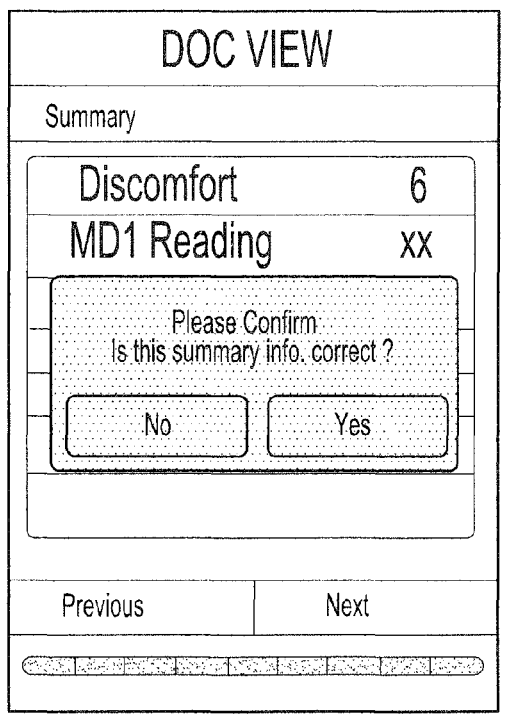
FIG. 39 is an illustrative example of a screen providing a questionnaire to a patient to confirm or not confirm whether or not a summary of clinical data input by the patient and data from at least one medical device are correct and therefore allowing the patient the option to make a change if required.
Figure 40:
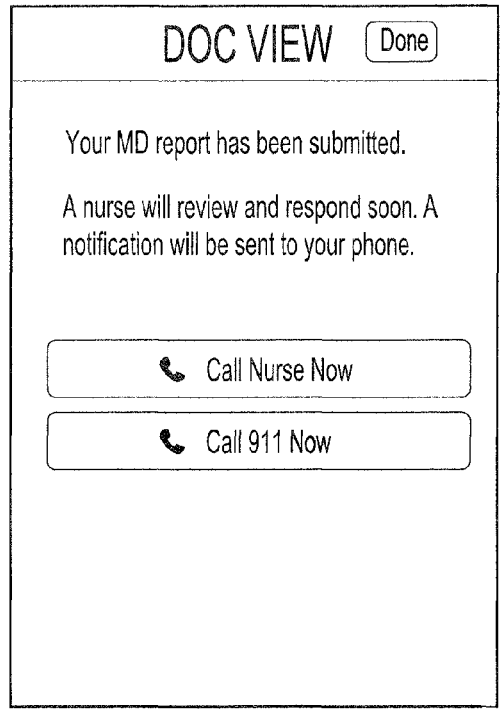
FIG. 40 is an illustrative example of a screen showing a medical device report has been submitted through an outside third party and providing the patient an opportunity to send a message or to make a phone call.

Such a screen as shown in FIG. 38 affords for the patient to change and/or edit subjective data if he or she sees that a mistake has been made. In addition, FIG. 39 illustrates a screen that affords for the patient to confirm whether or not the summary information is correct and if the information is correct, submit the data to a clinician. Once the report has been submitted, a confirmation is provided as shown in FIG. 40.

With respect to the readings shown in FIG. 38, it is appreciated that a subjective reading such as discomfort would naturally be input by the patient but that the medical device readings could be directly transferred from the medical device to the portable wireless device, from the download device 400 to the portable wireless device, and/or a combination thereof. In the alternative, the patient can take a reading from a medical device and input the reading into the portable wireless device manually.

Figure 41:
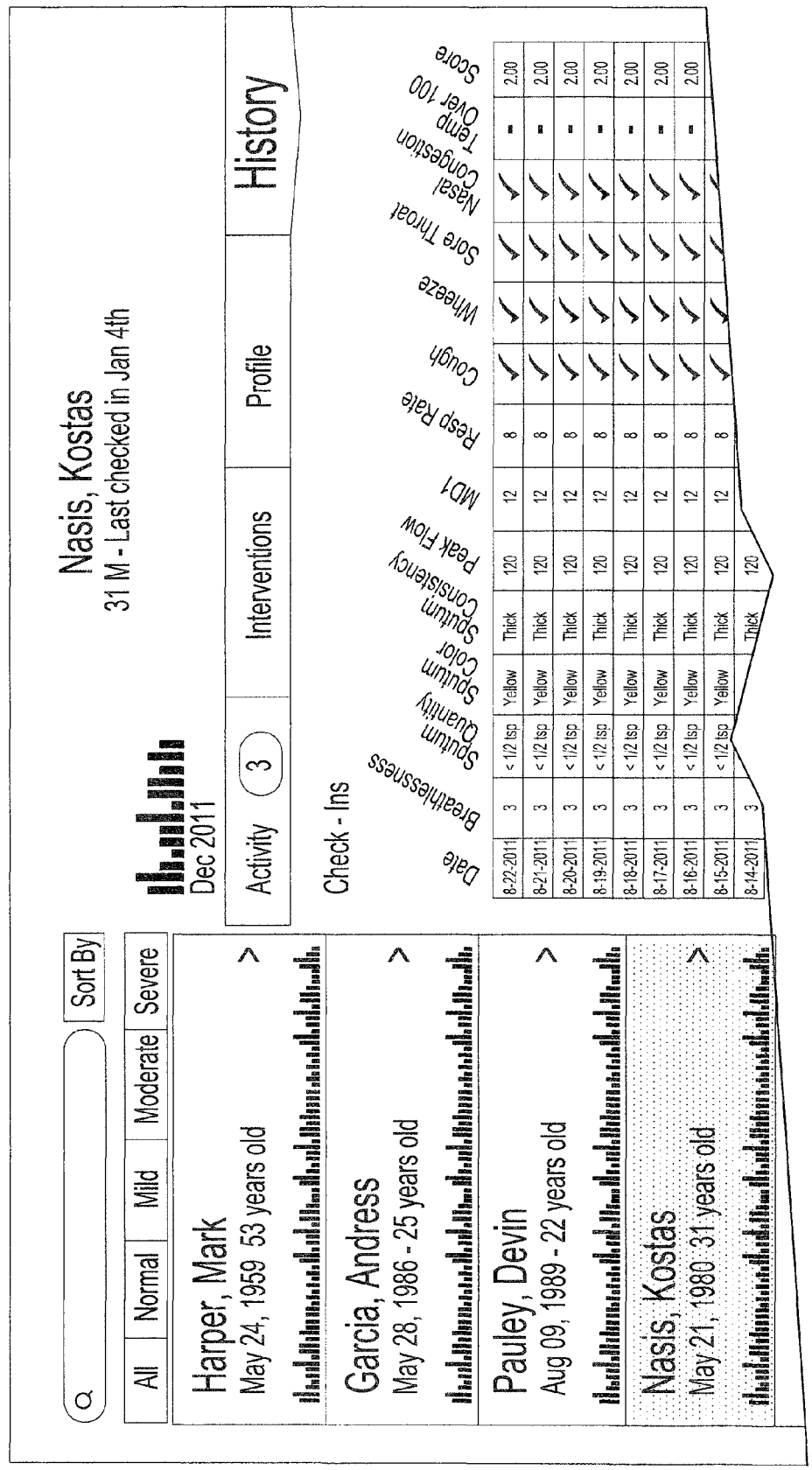
FIG. 41 is an illustrative example of a screen for a clinician dashboard showing a summary of patient input data and medical device data and level of severity for one or more patients.

The data, summary, report, and the like can be wirelessly transmitted to the web-based portal or servers 210 as described with respect to FIG. 1, which can be accessed by a clinician and analyzed and/or compared by or to a clinical study, an algorithm, decision tree, etc., made available on the database servers 220. For example, FIG. 41 shows a screenshot of, e.g. a smart tablet, which has a series of patient records and data for a COPD disease and a medical device (MD1). Similar to the discussion with respect to FIG. 17, FIG. 41 and the system affords options on how to sort (Sort By button) through the patients and/or the data, for example selecting All of the patients, only patients having a normal level of wellness with respect to COPD, and/or medical device reading.

Figure 42:
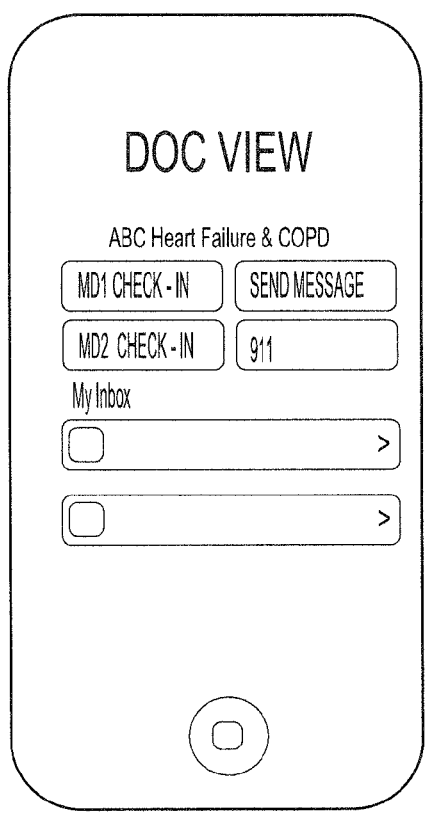
FIG. 42 is an illustrative example of a patient entry screen for a medical device application according to an embodiment of the present invention.
Figure 43:
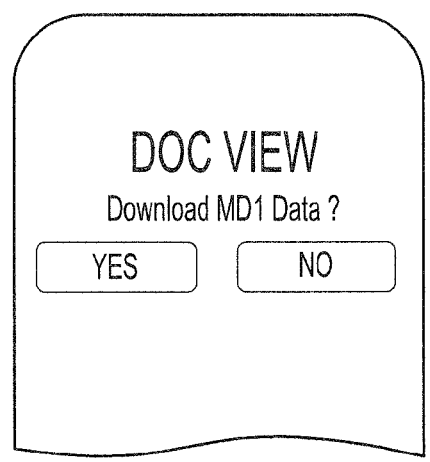
FIG. 43 is an illustrative example of a screen asking a patient whether or not they wish to download medical device data.
Figure 44:
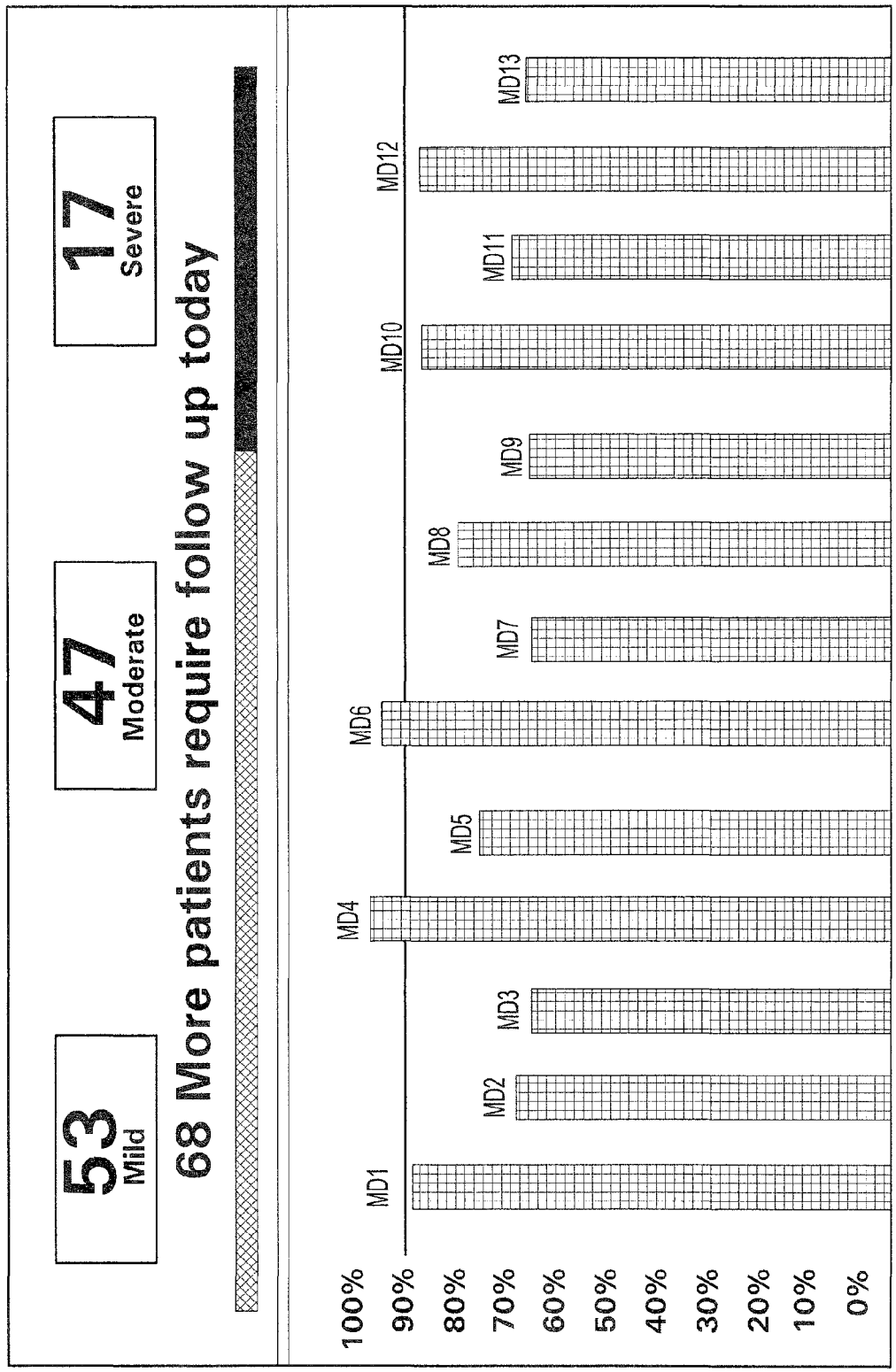
FIG. 44 is an illustrative example of a clinician reporting screen for a patient or a group of patients illustrating how many patients having medical devices have been seen or have reported their conditions and/or medical device data, and how many more patients need to be followed up with according to an embodiment of the present invention.

Referring to FIG. 42, an illustrative screen is shown for checking in with respect to one or more medical devices, sending a message and/or a call to 911. Furthermore, FIG. 43 illustrates a screen for downloading medical device data either to the portable wireless device itself or to the web-based portal or servers 210 which can be accessed by a clinician and analyzed and/or compared by or to a clinical study, an algorithm, decision tree, etc. made available on the database servers 220. Finally, FIG. 44 provides an illustrative example of a clinician reporting screen for a plurality of medical devices being used by patient or a group of patients illustrating how many patients have been seen or reported, their conditions, and how many more patients need to be followed up with. In addition, the screen illustrates how a health care institution such as a hospital is doing based on specific ACO metric guidelines.

In this manner, a range of medical devices can be monitored remotely and allow for interactive monitoring with a patient to provide preventive health care with "expert" or "smart" analysis of medical device and/or patient input data and thereby reduce re-admission trips to the hospital and the like. In addition, the system can provide advertising and education to the patient based on their specific illnesses, particular medical device they are using, and baseline data. For example, if the patient has a history of smoking, drinking, etc., the system can inquire if the patient is smoking, has started smoking again, is drinking excessively, and the like, and based on the answer from the patient, provide education on smoking cessation programs, the harmful effects of smoking, the harmful effects of excessive drinking, and the like. Furthermore, the system could provide advertising as to health care aids, equipment, and the like that may be useful to the patient with respect to a particular disease they have. It is appreciated that the advertising and/or education materials can be stored in the servers 200 and/or be made available via Internet links, Internet cloud storage, etc.

It should be appreciated that the above disclosure is a representation of the system and that modifications to the system will be obvious to those skilled in the art. For example, additional diseases, questions for patients to answer, etc., not specifically discussed herein can fall within the scope of the invention. Illustratively, questions related to swelling of a patient's joints, extremities, and the like can be included. As such, the above embodiments, examples, etc. are not to be restrictive on the scope of the invention but should be interpreted broadly. As such, it is the claims and all equivalents thereof that define the scope of the invention.

We claim:

1. A process for improving medical device management for a patient, the process comprising:
    providing a plurality of portable wireless devices to a plurality of patients that having a plurality of medical devices such that each of the plurality of patients have one of the medical devices and one of the portable wireless devices, each of the plurality of wireless devices having an electronic control unit (ECU), memory and an interactive remote patient monitoring module (IRPMM) for at least one medical device, the plurality of portable wireless devices each operable to transmit and receive information to/from an outside third party, the IRPMM having a medical device data request module operable to request and receive subjective data input from the patient and medical device data related to the at least one medical device input from the patient or automatically receive medical device data without input from the patient;
    providing a clinical data analysis module with at least one assessment tool selected from a group consisting of a web-based assessment tool, clinical guidelines, health risk assessments, a pharmaceutical protocol, a best practice for the at least one disease, an algorithm and a decision tree, the clinical data analysis module operable to receive the subjective and medical device data from each of the plurality of patients, generate a score for each received subjective and medical device data from each of the plurality of patients and provide a certified decision and/or protocol as a function of the medical device data input from the patient;
    requesting information related to the medical device from each of the plurality of patients using the IRPMM;
    each of the plurality of patients inputting subjective data related to the medical device into the IRPMM of the portable wireless device that each patient has;
    transmitting the input subjective and medical device data input by the patient or automatically received medical device data to the clinical data analysis module, the clinical data analysis module providing a certified decision and/or protocol and a score for each patient as a function of the medical device data;
    evaluation of the input subjective data and medical device data from each patient as a function of the score for each patient by a clinician, the clinician accepting or changing the certified decision and/or protocol;
    transmitting the accepted or changed certified decision and/or protocol for each patient to the patient's portable wireless device; and
    each patient receiving the accepted or changed certified decision and/or protocol from the clinician.

2. The process of claim 1, wherein the medical device data request module has one or more data input queries related to the at least one medical device, the medical device data request module operable to request data from the at least one medical device.

3. The process of claim 2, wherein the at least one medical device is a Food and Drug Association (FDA) approved medical device.

4. The process of claim 3, wherein the FDA approved medical device is a Class II medical device.

5. The process of claim 3, wherein the FDA approved medical device is a Class III medical device.

6. The process of claim 5, wherein the medical device data analysis module has a module to provide a level of measurement operable to provide an indication of operation of the at least one medical device as a function of the received medical device data from the at least medical device and the at least one assessment tool.

7. The process of claim 6, wherein the system is operable to compare the indication of operation to a standard intervention protocol based on a baseline of the patient or the at least one medical device.

8. The process of claim 1, furthering comprising providing an end-to-end chain of custody visual notification operable to show a chain of custody for a given medical device data reporting event.

9. The process of claim 8, wherein the end-to-end chain of custody visual notification is operable to show a completed step in a Pending Initial Data Review—Treatment Recommended—Treatment Reviewed and Approved—Approved Treatment Sent to Patient—Patient Acknowledges Receipt chain of custody for the given medical device data reporting event.

10. The process of claim 9, wherein the system is monitoring the patients' activity and notifies a named party or parties that a specified event did or did not take place; and wherein the system makes an action occur is at least an SMS/Text message, a phone call, a fax, an email, a page to notify the named party or parties that the specified event did, or did not, take place indicating an action is required.

* * * * *